(12) United States Patent  
Hillendahl et al.

(10) Patent No.: US 7,310,462 B2
(45) Date of Patent: Dec. 18, 2007

(54) BIOCHEMICAL ASSAY DETECTION IN A LIQUID RECEPTACLE USING A FIBER OPTIC EXCITER

(75) Inventors: James W. Hillendahl, Vacaville, CA (US); David E. Waldbeser, Martinez, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 11/583,409

(22) Filed: Oct. 18, 2006

(65) Prior Publication Data

US 2007/0263954 A1 Nov. 15, 2007

Related U.S. Application Data

(63) Continuation of application No. 10/252,023, filed on Sep. 19, 2002, now Pat. No. 7,218,810.

(60) Provisional application No. 60/325,855, filed on Sep. 27, 2001, provisional application No. 60/325,876, filed on Sep. 27, 2001.

(51) Int. Cl.
   *G02B 6/32* (2006.01)
   *G01N 1/10* (2006.01)

(52) U.S. Cl. ............................ 385/33; 385/31; 385/38; 356/246

(58) Field of Classification Search .................... None
   See application file for complete search history.

(56) References Cited

U.S. PATENT DOCUMENTS 4,626,684 A 12/1986 Landa (Continued)

FOREIGN PATENT DOCUMENTS

GB   2196734 A   5/1988

(Continued)

OTHER PUBLICATIONS

Jing, W. "NA of the single mode fiber," at <<http://laser.physics.sunysb.edu/~wjing/presentation/>> visited on Jul. 24, 2002, 7 pages total.

(Continued)

*Primary Examiner*—Sung Pak
(74) *Attorney, Agent, or Firm*—Townsend and Townsend and Crew LLP

(57) ABSTRACT

Biochemical assays that are performed in cuvettes and in the wells of multi-well plates and that utilize excitation and light emission as labels for detection are enhanced by an illumination and detection system that supplies excitation light through an optical fiber that transmits excitation light from an excitation light source to the cuvette or well. Emission light produced by the excitation is then collected by a collimating lens and converted to a signal that is compiled by conventional software for analysis. The optical fiber and collimating lens can either be on the same side of the receptacle (generally the open side) or on opposite sides, i.e., one above and the other below. When the optical fiber and the collimating lens are both on the open side of the receptacle, they are arranged such that the direction of travel of the excitation light and the direction along which the emission light is collected are not coaxial, and preferably both are at an acute angle to the axis normal to the mouth of the receptacle. Illumination systems are also disclosed in which a ultraviolet, visible, or near-infrared light source is optically coupled to an optical fiber.

14 Claims, 2 Drawing Sheets

U.S. PATENT DOCUMENTS

| | | |
|---|---|---|
| 5,116,759 A | 5/1992 | Klainer et al. |
| 5,436,718 A | 7/1995 | Fernandes et al. |
| 5,459,803 A | 10/1995 | Yamane et al. |
| 5,578,818 A | 11/1996 | Kain et al. |
| 5,645,800 A | 7/1997 | Masterson et al. |
| 6,016,195 A | 1/2000 | Peters |
| 6,097,025 A | 8/2000 | Modlin et al. |
| 6,188,813 B1 | 2/2001 | Dourdeville et al. |
| 6,232,068 B1 | 5/2001 | Linsley et al. |
| 6,362,004 B1 | 3/2002 | Noblett |
| 6,399,952 B1 | 6/2002 | Maher et al. |
| 6,407,858 B1 | 6/2002 | Montagu |
| 6,488,892 B1 | 12/2002 | Burton et al. |
| 6,542,231 B1 | 4/2003 | Garrett |
| 2001/0033381 A1 | 10/2001 | Stumbo et al. |
| 2002/0171836 A1 | 11/2002 | Gerner et al. |
| 2003/0059855 A1 | 3/2003 | Cunningham et al. |
| 2004/0038390 A1 | 2/2004 | Boege et al. |

FOREIGN PATENT DOCUMENTS

| | | |
|---|---|---|
| JP | 55125436 | 9/1980 |
| WO | WO 00/62549 A1 | 10/2000 |

OTHER PUBLICATIONS

La Rosa, A.H. et al. "Optical imaging of carrier dynamics in silicon with subwavelength resolution," *Appl. Phys. Lett.* Mar. 1997, pp. 1656-1658, vol. 70, No. 13.

BIOCHEMICAL ASSAY DETECTION IN A LIQUID RECEPTACLE USING A FIBER OPTIC EXCITER

CROSS-REFERENCE TO RELATED APPLICATIONS

This application is a Continuation of U.S. application Ser. No. 10/252,023 filed Sep. 19, 2002 now U.S. Pat. No. 7,218,810, which is an application claiming the benefit under 35 USC 119(e) of U.S. Provisional Application Ser. No. 60/325,855 filed Sep. 27, 2001, and U.S. Provisional Application Ser. No. 60/325,876 filed Sep. 27, 2001.

This application claims the benefits of U.S. provisional patent applications Nos. 60/325,855 and 60/325,876, both filed on Sep. 27, 2001, for all purposes legally capable of being served thereby. The contents of each of these provisional patent applications are incorporated herein by reference in their entirety, as are all other patent and literature references cited throughout this specification.

BACKGROUND OF THE INVENTION

1. Field of the Invention

This invention resides in the field of biochemical assays performed in receptacles such as cuvettes or the wells of multi-well plates such as MICROTITER® plates, and particularly in obtaining the assay results by optical excitation of the receptacle contents and detection of the emissions resulting from the excitation.

2. Description of the Prior Art

Fluorescence and other optical signals are widely used in biochemical assays, particularly as a label in distinguishing test species that have demonstrated a sought-after property or characteristic in the assay from those that have not. Assays utilizing optical signals are frequently performed in liquid or fluid media retained in a sample receptacle, and optical measurements are performed either on species suspended in the liquid media or on species adhering to the walls of the receptacle, such as species immunologically bound to the walls of microplate wells or cells plated to the bottoms of cuvettes. Instrumentation in current use for measuring fluorescence include a light source and a lens system for focusing a beam into the sample receptacle, and an optical system for collecting and processing the emission light that results from the excitation. The two frequently interfere with each other, however, resulting in a loss of assay sensitivity.

In one type of excitation and emission detection system, a pierced mirror, which is either flat or elliptical, is used for both directing the excitation light to the sample receptacle and collecting the emission light that is produced. Pierced-mirror systems have limited sensitivity, however, since the need to optimize the collection of the weaker emission light requires compromises that result in loss of much of the excitation light. As a result, these devices suffer from a reduced intensity due to restricted aperture considerations and to the misdirection of a portion of the excitation light.

Other systems use a dichroic mirror to separate the excitation and emission light which are otherwise along a common path. The use of a dichroic mirror simplifies the optical path and instrument layout, but efficient separation of the emission light from the excitation light requires an expensive optical filter and a reduction in the signal light. Dichroic mirror systems are principally used in microscopy where light is abundant, rather than in systems where trace amounts of fluorophore are detected with low levels of emission light.

SUMMARY OF THE INVENTION

The present invention resides in illumination and detection systems for biochemical assays performed in small liquid receptacles such as cuvettes, small test tubes, or the wells of a multi-well plate. The receptacle is illuminated with a divergent beam of excitation light from an optical fiber, and emission light generated in the receptacle as a result of the excitation is collected, preferably without the use of an optical fiber, by a collimating lens and converted by a detector to a signal that can be quantified, recorded, and otherwise processed by conventional instrumentation components. When the receptacle is one well of a multi-well plate such as a MICROTITER® plate, further signals are obtained by rastering either the plate or the optical system until detection has been performed on all wells of the plate. This system is applicable to any receptacle in which an assay is performed that utilizes a label that emits a signal upon optical excitation. Preferred labels are fluorophores and fluorescent emissions, but the invention extends as well to phosphors and other types of optically excitable labels known to those familiar with biochemical assays.

In preferred embodiments of the invention, the optical system is arranged such that the direction of travel of the excitation light and the direction along which the emission light is collected are two different directions, i.e., the two paths do not have a common axis. The optical fiber is configured to illuminate the test area either by epi-illumination (i.e., directing excitation light to the receptacle contents through the open mouth of the receptacle and collecting emission light through the open mouth as well) or by trans-illumination (using a light-transmissive receptacle or one with a light-transmissive floor, and either directing excitation light to the receptacle from above and collecting emission light from below through the light-transmissive floor, or directing excitation light from below through the light-transmissive floor and collecting emission light from above). In multi-well plates, illumination and emission detection can likewise occur at opposite sides of the plate, either by illuminating from below (the underside of the plate) and collecting emission from above (through the mouth of a well), or by illuminating from above and collecting emission from below. In systems utilizing epi-illumination, the optical fiber and the direction along which the emission light is collected are not coaxial, instead forming an angle to each other. In trans-illumination as well, the optical fiber and the optical path used for collection of the emission light are in a non-coaxial arrangement. Preferred optical fibers for use in this invention are those that produce a divergent angle sufficient to illuminate the entire receptacle including all of the test materials contained in the receptacle, and to illuminate only that receptacle, i.e., without illuminating materials in neighboring receptacles.

Preferred excitation light sources are those supplying ultraviolet, visible, or near-infrared light, optically coupled with the optical fiber so that substantially all of the light from the light source enters the fiber for transmission to the receptacle interior. This will result in substantially no loss of intensity between the light source and the receptacle. The optical fiber itself may be a simple fiber or one that includes such elements as a collimator or optical filter, or a collimator-filter-collimator assembly, to process the light in various ways that will enhance its use for particular applications and assays.

Systems in accordance with this invention offer numerous advantages over the prior art. By separating the excitation and emission light paths, systems in accordance with this invention limit the excitation and emission optics to a single function each, thereby permitting individual optimization of these two optical systems. In epi-illumination systems, little of the excitation light is detected in the emission light path and a maximal signal-to-noise ratio is achieved, particularly when the illumination fiber and the emission collection optics are at different angles relative to the normal axis. When the system is used on multi-well plates, only a single well is illuminated by the optical fiber and emission is collected from that well individually, thereby eliminating crosstalk and maximizing the signal of that well. This leads to maximal signal collection and superior performance for any given level of detection and sensitivity. Furthermore, excitation systems of this invention require no additional lenses or other optical elements between the excitation fiber and the assay receptacle, and can thus avoid the losses in light intensity that are often caused by these additional elements. In aspects of this invention that are directed to an optical fiber optically coupled directly to an LED or SLD light source, the coupled product is inexpensive, durable, and compact, and delivers bright light while generating minimal heat. This simplified yet highly efficient design presents advantages for packaging, cost and size reduction.

DETAILED DESCRIPTION OF THE INVENTION AND PREFERRED EMBODIMENTS

Figure 1:
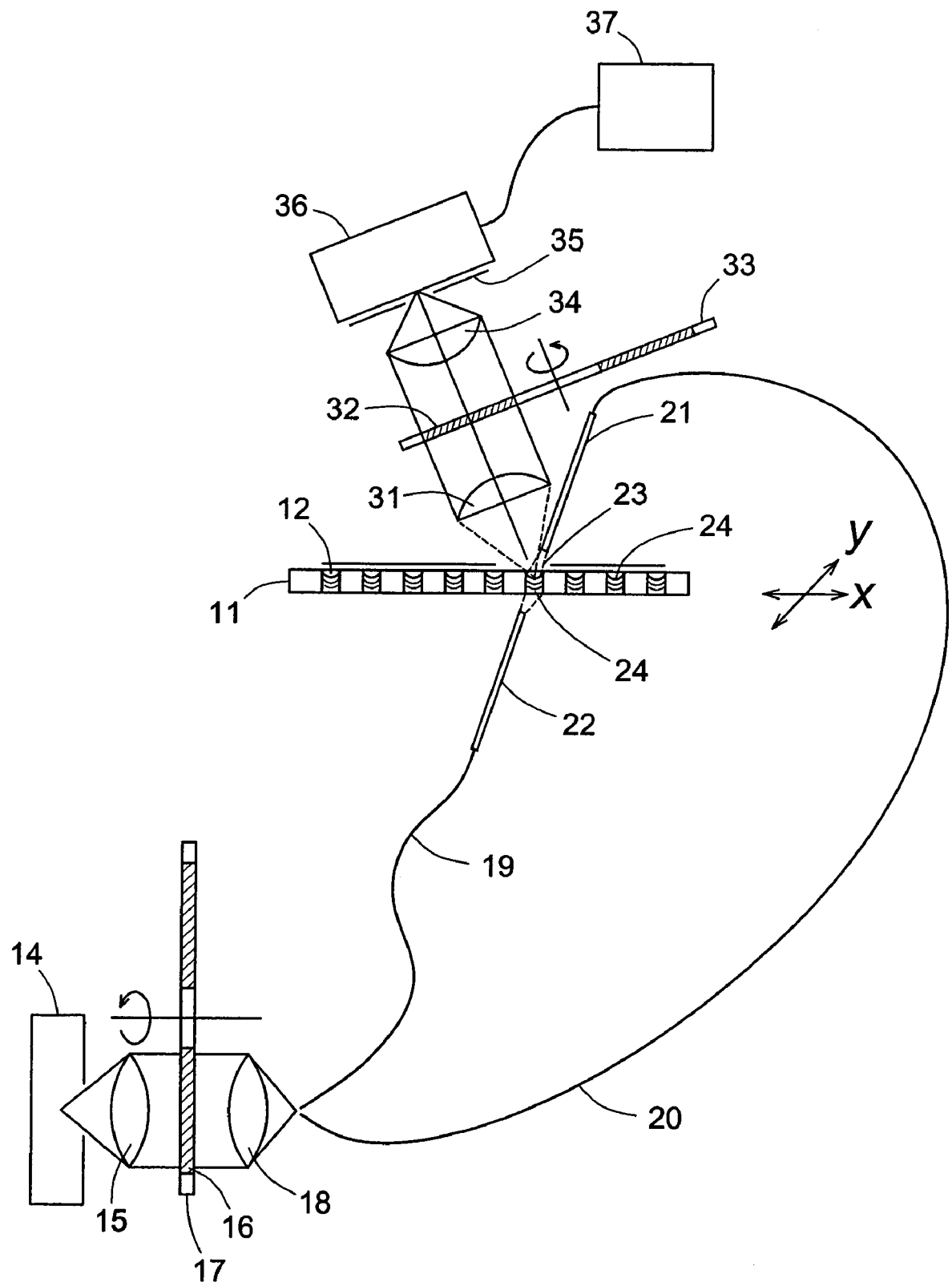
FIG. 1 is a diagram of an excitation and detection system for a multi-well plate utilizing the features of the present invention.

Receptacles in which bioassay detection can be performed by use of the present invention include cuvettes, small test tubes, wells of multi-well plates, and any variety of vessels capable of containing the components used in performing biochemical assays. Examples of multiwell plates are MICROTITER® plates, as well as plates bearing different designations but generally containing either a row of wells or a two-dimensional rectangular array of wells. The most commonly used multi-well plates are those with a 96-well (12×8) array. Others have 6-well, 12-well, 48-well, 384-well, and 1536-well arrays. Typical well diameters or widths are from about 4 mm to about 40 mm, and preferably from about 4 mm to about 11 mm. The emissions to be generated and detected in the practice of this invention can arise from liquid retained in the receptacle, from substances suspended in the liquid, or from substances adhering to the receptacle walls.

The excitation system of this invention may contain any of a variety of different types of light sources. Examples are broadband light sources such as xenon flash lamps, quartz halogen lamps, light-emitting diodes (LEDs), vertical cavity surface-emitting lasers (VCSELs), superluminescent diodes (SLDs), and narrowband sources such as single or multiple discrete wavelength lasers. In preferred systems, the light source is optically coupled to the optical fiber. For point sources of light or sources such as solid state sources that are nearly point sources, optical coupling may be achieved by proximity coupling. Otherwise, a coupling lens or lens system that will transmit substantially all of the light from the light source to the fiber can be used. The system can also include an optical excitation filter, a monochromator, or a tunable acousto-optic filter. The optical fiber transmits light from the light source to the receptacle to excite either a single label or multiple labels that are present in the receptacle. Emission light resulting from the excitation is collected by a collimating lens system which directs the light to a detector, optionally first passing through an optical emission filter, a monochromator, or a tunable acousto-optic filter. Examples of suitable detectors are photomultiplier tubes, microchannel plates, silicon PIN diodes, avalanche photodiodes (APDs), CCD detectors, and CMOS detectors.

The optical fiber is either straight or tapered along its length. The choice of fiber may vary with the particular type of receptacle to which the light is directed. A multi-mode fiber with cladding and outer buffer coating is preferred, particularly one with a divergence angle suitable for filling the interior of the receptacle. Such fibers are commercially available from various suppliers well known to those in the industry. One such supplier is 3M Company, St. Paul, Minn., USA, and another is Polymicro Technologies, LLC, Phoenix, Ariz., USA.

The optical fiber can have either a standard tip or a shaped tip on either or both of its ends, or a combination of both. In certain embodiments of the invention, the delivery end preferably has a shaped tip such as a concentrator cone tip. The tip may also have an integral lens. The divergence angle at the distal tip is preferably within the range of about 10 degrees to about 60 degrees, most preferably from about 10 degrees to about 20 degrees. In terms of the numerical aperture (the sine of the divergence angle $\theta$), the preferred range is from about 0.17 to about 0.94, and most preferably from about 0.17 to about 0.34. For MICROTITER® plates, a presently preferred numerical aperture is 0.22 (a divergence angle of 12.7 degrees). Optical fibers with shaped tips as described in this paragraph are available from Polymicro Technologies referenced above.

The tip of the optical fiber is preferably placed very close to the mouth of the receptacle, particularly in the case of receptacles that are wells in multi-well plates where illumination of neighboring wells is sought to be avoided. Preferably, the fiber tip is placed within 1 mm to 10 mm of the mouth of the well.

The vessel in which the receptacle is formed can be opaque or light-transmissive, and light-transmissive vessels can be translucent or transparent. When a light-transmissive vessel is used, illumination of the receptacle interior with excitation light can be achieved from the underside of the vessel, i.e., through the light-transmissive bottom of the vessel ("trans-illumination"). The angle of incidence of the excitation light is defined relative to the axis normal to the mouth of the receptacle, and this angle is not critical and may vary. Likewise, the direction along which the collimating lens collects the emission light can vary. In systems where trans-illumination is used, it is preferred that the emission light be collected along an acute angle relative to the axis. Preferred such angles are at least about 5° and most preferably from about 5° to about 15°. In systems involving epi-illumination, the optical fiber and the direction along which the emission light is collected are non-coaxial, and it is preferred that the fiber and the emission collection direction each form angles (relative to the axis) of from about 5° to about 60°, and more preferably from about 50 to about 25°. When the receptacle is a multi-well plate, a presently preferred angle for the optical fiber (relative to the axis) in epi-illumination systems is 10°, with the emission collection path at 15° relative to the fiber, while in trans-illumination systems a presently preferred angle for the optical fiber is 5-10° (relative to the axis), with the emission collection path along the axis itself.

Of the various types of light sources that can be used in the practice of this invention, broadband LEDs are preferred. This and other types of light source can also include a phosphor or other broadband conversion element upstream of the coupling to the fiber. The conversion element can be a coating on the light source, or it can be incorporated into the plastic packaging of the light source or in a gel or other discrete closed package. As a further alternative, the conversion element can be intagliated into the end of the fiber itself.

The optical coupling between the light source and the optical fiber can be achieved by a focusing lens or lens system located between the light source and the optical fiber, or by direct coupling of the optical fiber to the light source. Examples of focusing lens systems are a ball lens, a pair of microscope objectives, and a condenser pair of plano convex lenses. Proximity coupling, i.e., direct coupling of the fiber to the light source, is preferred. LEDs and SLD'S, which are readily available from commercial suppliers, can be readily modified by removing the lens system supplied by the manufacturer and placing the flat fiber end very close to, and preferably in direct secured contact with, the glowing LED itself. An optically clear cement with low autofluorescence can be used. Examples of such a cement are Norland Optical Cement NOA 73 and NOA 61, Norland Products, Inc., Cranbury, N.J., USA. Alternatives to cements are gels or oils that are optically clear. To stabilize the coupling, the LED or SLD and the fiber end can be encased in a metal tube, a straight tip (ST) connector, or any other packaging, with one end of the connector joined to the LED or SLD and the other to the optical fiber.

While the novelty-defining concepts and features of the invention can be implemented in many different configurations and arrangements, a convenient way to achieve an understanding of these features is to study individual systems within the scope of the invention. Such system are depicted in the Figures.

The system shown in FIG. 1 is arranged for signal generation and detection in a multi-well plate 11 such as a MICROTITER® plate, each well 12 of which is partially filled with liquid components of a biochemical assay. The contents of each well have been treated with any of various fluorochrome dyes or probes or any other labels that when irradiated with an excitation light beam respond by producing emission light. The well diameter can be less than 4 mm or greater than 36 mm in diameter, depending on the number of wells in the plate. The plate 11 is held by a holding fixture (not shown) which moves or rasters the plate in the x and y directions within a plane that is transverse to the direction of the optical paths through which excitation and emission collection are performed. This rastering movement enables the system to capture signals sequentially from the entire array of wells. As an alternative arrangement, the plate can be held stationary and the optics made movable in the x and y directions across the sample surface.

An excitation light source 14, which may be a broadband source such as for example a xenon lamp, a quartz halogen lamp, an LED, an SLD, or a narrow band source such as for example a single or multiple discrete wavelength laser, illuminates a collimating lens 15. Alternatively, two or more discrete lasers can be used simultaneously with a single fiber. The collimated light emerging from the collimating lens 15 passes through an optical excitation filter 16 on a multi-position filter wheel 17. The filter wheel permits the selection of particular excitation wavelengths from a variety of wavelengths, and its rotation and position can be controlled by software appropriately adapted to particular experimental protocols. As alternatives to the optical excitation filter, a monochromator or a tunable acousto-optic filter may be used. A second lens 18 focuses the light and couples it into either of two optical fibers 19, 20. The fibers terminate in fiber holders 21, 22, respectively, the output end of each fiber holder being positioned in close proximity to a well 12 on the plate 11. These two optical fibers offer alternative means of providing excitation light to the well, one fiber 21 delivering the excitation light to the top side of the plate through the open mouth 23 of the well for epi-illumination and the other fiber 22 delivering the excitation light to the underside 24 of the plate for trans-illumination of the well through the plate itself.

In the system shown in FIG. 1, no additional lenses or optics are located between the fiber holders 21, 22 and the well plate 11. Light from the fiber tip 23 produces a cone-shaped beam of excitation light which fills the well 12. The divergence of the light cone can also be controlled or modified by either specialized cutting, polishing, or angling of the fiber end. Optionally, a mask 24 can be positioned above the sample to further assure that the well of interest does not receive any stray excitation or emission light from neighboring wells or from dust or other contaminants.

The emission light that the well 12 emits upon excitation is collected by a collimating lens 31, and the collimated emission light passes through an optical emission filter 32 on a multi-position filter wheel 33. Alternatively, a monochromator or tunable acousto-optic filter can be used in place of the optical emission filter 32. A second lens 34 then focuses the collimated light through an aperture 35 to control stray light and onto a light detector 36. Examples of suitable light detectors are photomultiplier tubes, silicon PIN diodes, avalanche photodiodes (APDs), CCD detectors, and CMOS detectors. The detector 36 registers the emission light intensity and sends an output signal to a recorder or to processing and control electronics 37.

These systems and other systems within the scope of this invention are readily adaptable to achieve signal generation and processing by Time-Resolved Fluorescence. This is accomplished for example by using a flashlamp, an LED, or an SLD as the light source, imposing a controlled delay time between a flash of the light source and the signal collection, and allowing for programmable variable signal collection integration time. The only modifications needed to achieve this are modifications of the software and electronics, and such modifications will be readily apparent to those skilled in the art of Time-Resolved Fluorescence.

Although not shown in the drawings, the system can include two or more optical excitation fibers arranged either in a linear array or an x-y (two-dimensional) array rather than in a single fiber. Each individual excitation fiber is associated with a separate collection channel, and the entire fiber array can be moved across the well plate, or the plate moved relative to the fiber array, and in either case signals are obtained from all wells of the plate in a shorter span of time than a single fiber.

Figure 2:
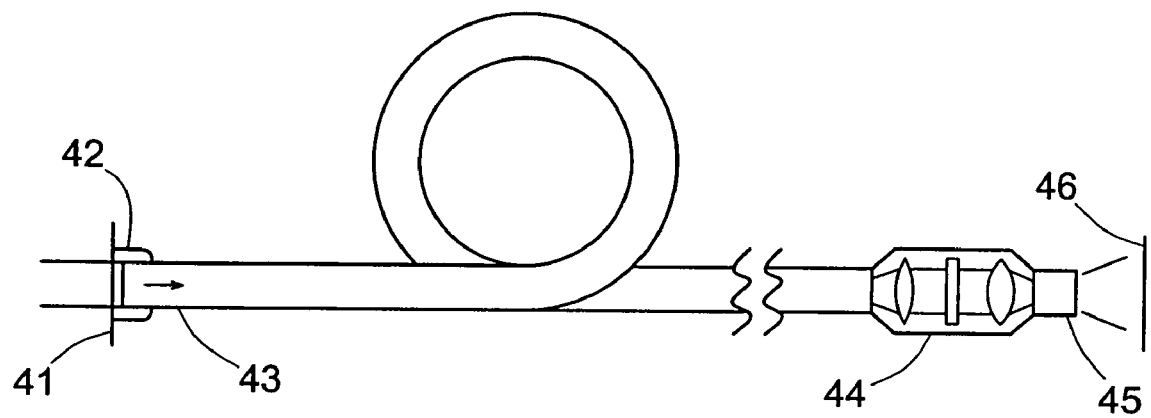
FIG. 2 is a diagram of an excitation system for use in conjunction with the excitation and detection system of FIG. 1, using an LED or SLD light source optically coupled to the fiber and an optical filter on the output end of the fiber.
Figure 3:
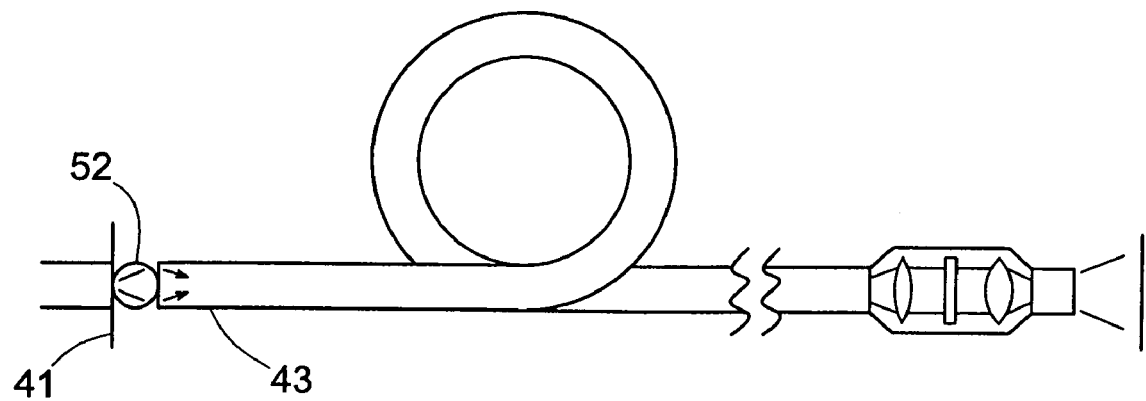
FIG. 3 is a diagram of a second excitation system for use in conjunction with the excitation and detection system of FIG. 1, also using an LED or SLD light source optically coupled to the fiber and an optical filter on the output end of the fiber.

Examples of illumination systems in accordance with this invention utilizing an LED or SLD light source are shown in FIGS. 2 and 3.

The system of FIG. 2 includes an LED or SLD source 41, preferably a white light LED or SLD, directly coupled to the flat end of an optical fiber 43 through an optical cement such as those described above. The coupling is surrounded by an epoxy potting compound 42 or a ring or tube. Light emerging from the LED or SLD is efficiently collected by the optical fiber 43 and transmitted to a fiber-optic device 44, which consists of a first fiber collimator for the light emerging from the LED or SLD, an optical bandpass filter, and a second fiber collimator for the light emerging from the optical bandpass filter. The filter can either be a single optical bandpass filter or multiple filters mounted on a wheel or slide, allowing the user, either manually or by automated means, to select a particular filter and thereby excite a specific fluorophore. The light emerging from the second fiber collimator returns to the fiber for delivery from the fiber tip 45 to a test region 46 on a multi-well plate.

The system of FIG. 3 has the same components as the system of FIG. 2 except that the sealant and packaging 42 of FIG. 1 are replaced by a compact lens or lens system 52.

The foregoing descriptions are offered primarily for purposes of illustration. Further modifications, variations and substitutions that still fall within the spirit and scope of the invention will be readily apparent to those skilled in the art.

What is claimed is:

1. Apparatus for generating and detecting an optical signal from a reaction mixture resulting from a bioassay performed therein, said apparatus comprising:
   a liquid receptacle;
   an excitation light source;
   an optical fiber from which light emerges as a divergent beam, said optical fiber arranged to transmit excitation light from said excitation light source and to cause said divergent beam to directly enter said receptacle so as to entirely illuminate any sample that may be present in said receptacle;
   a light collecting lens arranged to collect emission light from said receptacle; and
   detection means for receiving emission light collected by said light collecting lens and for generating a signal representative of said emission light thus collected;
   in which said receptacle has an open mouth, said optical fiber is arranged to direct said excitation light through said open mouth, and said light collecting lens is arranged to collect said emission light through said open mouth.

2. Apparatus in accordance with claim 1 in which said light collecting lens is arranged to collect said emission light along an emission collection path that is not coaxial with said optical fiber.

3. Apparatus in accordance with claim 2 in which said open mouth defines an axis normal thereto, and said optical fiber and said emission collection path each form an angle of from about 5 to about 60 relative to said axis.

4. Apparatus in accordance with claim 2 in which said open mouth defines an axis normal thereto, and said optical fiber and said emission collection path form an angle of from about 5 to about 25 relative to said axis.

5. Apparatus for generating and detecting an optical signal from a reaction mixture resulting from a bioassay performed therein, said apparatus comprising:
   a liquid receptacle;
   an excitation light source;
   an optical fiber from which light emerges as a divergent beam, said optical fiber arranged to transmit excitation light from said excitation light source and to cause said divergent beam to directly enter said receptacle so as to entirely illuminate any sample that may be present in said receptacle;
   a light collecting lens arranged to collect emission light from said receptacle; and
   detection means for receiving emission light collected by said light collecting lens and for generating a signal representative of said emission light thus collected;
   in which said receptacle has a light-transmissive floor and an open mouth opposite said light-transmissive floor, said optical fiber is arranged to transmit light to the contents of said receptacle through one of said light-transmissive floor and said open mouth, and said light collecting lens is arranged to collect said emission light through the other of said light-transmissive floor and said open mouth.

6. Apparatus in accordance with claim 5 in which said receptacle defines an axis normal to said open mouth, and said light collecting lens is arranged to collect said emission light at an angle of at least about 5 relative to said axis.

7. Apparatus in accordance with claim 5 in which said receptacle defines an axis normal to said open mouth, and said light collecting lens is arranged to collect said emission light at an angle of from about 5 to about 15 relative to said axis.

8. Apparatus for generating and detecting an optical signal from a reaction mixture resulting from a bioassay performed therein, said apparatus comprising:
   a liquid receptacle;
   an excitation light source;
   an optical fiber from which light emerges as a divergent beam, said optical fiber arranged to transmit excitation light from said excitation light source and to cause said divergent beam to directly enter said receptacle so as to entirely illuminate any sample that may be present in said receptacle;
   a light collecting lens arranged to collect emission light from said receptacle; and
   detection means for receiving emission light collected by said light collecting lens and for generating a signal representative of said emission light thus collected;
   in which said liquid receptacle is a well of a multi-well plate, and said apparatus further comprises means for rastering either said multi-well plate relative to said optical fiber and said collimating lens or said optical fiber and said collimating lens relative to said multi-well plate until light from said excitation light source has illuminated, and emission light has been collected from, all wells of said multi-well plate.

9. A method for generating and detecting an optical signal from the contents of a reaction mixture resulting from a bioassay performed in said reaction mixture, said method comprising:
   (a) illuminating the contents of a receptacle containing said reaction mixture with light from an excitation light source through an optical fiber that produces a divergent emerging beam by directing the entire divergent beam into said receptacle so as to entirely illuminate any sample that may be present in said receptacle; and (b) collecting emission light from said receptacle by a light collecting lens and directing emission light thus collected to a detector;

in which said receptacle has an open mouth and said method comprises illuminating the contents of said receptacle through said open mouth and collecting said emission light from said receptacle through said open mouth.

10. A method in accordance with claim 9 in which step (b) comprises collecting said emission light from said receptacle along an emission collection path that is not coaxial with said optical fiber.

11. A method in accordance with claim 10 in which said receptacle defines an axis normal to said open mouth, and said optical fiber and said emission collection path each form an angle of from about 5° to about 60° relative to said axis.

12. A method in accordance with claim 10 in which said receptacle defines an axis normal to open mouth, and said optical fiber and said emission collection path form an angle of from about 5° to about 25° relative to said axis.

13. A method for generating and detecting an optical signal from the contents of a reaction mixture resulting from a bioassay performed in said reaction mixture, said method comprising:

(a) illuminating the contents of a receptacle containing said reaction mixture with light from an excitation light source through an optical fiber that produces a divergent emerging beam by directing the entire divergent beam into said receptacle so as to entirely illuminate any sample that may be present in said receptacle; and (b) collecting emission light from said receptacle by a light collecting lens and directing emission light thus collected to a detector;

in which said receptacle has a light-transmissive floor and an open mouth opposite said light-transmissive floor, step (a) comprises directing said divergent beam through one of said light-transmissive floor and said open mouth, and step (b) comprises collecting said emission light through the other of said light-transmissive floor and said open mouth.

14. A method in accordance with claim 13 in which said receptacle defines an axis normal to said open mouth, and step (b) comprises collecting said emission light along an emission collection path the forms an angle of 0 to about 15 relative to said axis.

* * * * *